US012745986B2

(12) United States Patent
Moehring et al.

(10) Patent No.: US 12,745,986 B2
(45) **Date of Patent: *Sep. 29, 2026**

(54) APPARATUS AND METHOD FOR CHARACTERIZATION OF A DUCTILE MEMBRANE, SURFACE AND SUB-SURFACE PROPERTIES

(71) Applicant: OtoNexus Medical Technologies, Inc., Bellevue, WA (US)

(72) Inventors: Mark A. Moehring, Seattle, WA (US); George A. Gates, Boerne, TX (US); Jay Chesavage, Palo Alto, CA (US); Rahul Singh, Carlsbad, CA (US)

(73) Assignee: OtoNexus Medical Technologies, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/947,945

(22) Filed: Nov. 14, 2024

(65) Prior Publication Data

US 2025/0228528 A1 Jul. 17, 2025

Related U.S. Application Data

(63) Continuation of application No. 18/298,136, filed on Apr. 10, 2023, now Pat. No. 12,167,936, which is a (Continued)

(51) Int. Cl.
*A61B 8/00* (2006.01)
*A61B 8/10* (2006.01)
(Continued)

(52) U.S. Cl.
CPC ................ *A61B 8/485* (2013.01); *A61B 8/10* (2013.01); *A61B 8/488* (2013.01); *A61B 8/5223* (2013.01);
(Continued)

(58) Field of Classification Search
CPC ........... A61B 8/485; A61B 8/10; A61B 8/488; A61B 8/5223; A61B 8/5292; A61B 3/165;
(Continued)

(56) References Cited

U.S. PATENT DOCUMENTS 4,442,715 A 4/1984 Brisken et al.
4,601,295 A 7/1986 Teele
(Continued)

FOREIGN PATENT DOCUMENTS

CN 104568736 A 4/2015
CN 108135539 A 6/2018
(Continued)

OTHER PUBLICATIONS

Co-pending U.S. Appl. No. 18/922,750, inventors Moehring; Mark A. et al., filed Oct. 22, 2024.
(Continued)

*Primary Examiner* — Sanjay Cattungal
(74) *Attorney, Agent, or Firm* — Wilson Sonsini Goodrich & Rosati

(57) ABSTRACT

An ultrasound signal processor uses an excitation generator to cause displacement of a membrane or surface while a series of ultrasound pulses are applied to the membrane or surface. Phase differences between a transmitted signal and received signal are examined to determine the movement of the membrane or surface in response to the applied excitation. An examination of the phase response of the membrane or surface provides a determination as to whether the fluid type behind the membrane or surface is one of: no fluid, serum fluid, or purulent fluid.

21 Claims, 6 Drawing Sheets

Related U.S. Application Data continuation of application No. 16/788,379, filed on Feb. 12, 2020, now Pat. No. 11,660,074, which is a continuation of application No. 15/173,615, filed on Jun. 4, 2016, now Pat. No. 10,675,001.

(51) Int. Cl.

| | |
|---|---|
| ***B06B 1/02*** | (2006.01) |
| *A61B 3/16* | (2006.01) |
| *B06B 1/06* | (2006.01) |

(52) U.S. Cl.
CPC .......... *A61B 8/5292* (2013.01); *B06B 1/0207* (2013.01); *A61B 3/165* (2013.01); *A61B 2503/40* (2013.01); *B06B 1/0292* (2013.01); *B06B 1/0644* (2013.01); *B06B 2201/76* (2013.01)

(58) Field of Classification Search
CPC . A61B 2503/40; B06B 1/0207; B06B 1/0292; B06B 1/0644; B06B 2201/76; G16H 50/30
See application file for complete search history.

(56) References Cited

U.S. PATENT DOCUMENTS

| | | | |
|---|---|---|---|
| 5,105,822 | A | 4/1992 | Stevens et al. |
| 5,178,147 | A | 1/1993 | Ophir et al. |
| 5,699,809 | A | 12/1997 | Combs et al. |
| 5,792,072 | A | 8/1998 | Keefe |
| 5,800,336 | A | 9/1998 | Ball et al. |
| 5,825,894 | A | 10/1998 | Shennib |
| 6,048,320 | A | 4/2000 | Brainard, II |
| 6,093,150 | A | 7/2000 | Chandler et al. |
| 6,312,379 | B1 | 11/2001 | Bradley et al. |
| 6,354,999 | B1 | 3/2002 | Dgany et al. |
| 6,951,127 | B1 | 10/2005 | Bi et al. |
| 7,107,159 | B2 | 9/2006 | German et al. |
| 7,440,117 | B2 | 10/2008 | Degertekin et al. |
| 9,074,976 | B2 | 7/2015 | Adolphi et al. |
| 9,482,646 | B2 | 11/2016 | Nagae et al. |
| 9,636,015 | B2 | 5/2017 | Hadba et al. |
| 9,726,647 | B2 | 8/2017 | Walker et al. |
| 10,660,604 | B2 | 5/2020 | Moehring et al. |
| 10,675,001 | B2 | 6/2020 | Moehring et al. |
| 11,627,935 | B2 | 4/2023 | Moehring et al. |
| 11,660,074 | B2 | 5/2023 | Moehring et al. |
| 12,167,934 | B2 | 12/2024 | Moehring et al. |
| 12,167,936 | B2 | 12/2024 | Moehring et al. |
| 2004/0015079 | A1 | 1/2004 | Berger et al. |
| 2004/0133108 | A1 | 7/2004 | Lewandowski |
| 2004/0167404 | A1 | 8/2004 | Bessler |
| 2005/0251042 | A1 | 11/2005 | Sandrin et al. |
| 2006/0070424 | A1 | 4/2006 | Saari et al. |
| 2007/0016050 | A1 | 1/2007 | Moehring et al. |
| 2007/0129632 | A1 | 6/2007 | Voie et al. |
| 2008/0021324 | A1 | 1/2008 | Seto |
| 2008/0051655 | A1 | 2/2008 | Sato et al. |
| 2009/0143656 | A1 | 6/2009 | Manwaring et al. |
| 2009/0143676 | A1 | 6/2009 | Matsumura |
| 2010/0048985 | A1 | 2/2010 | Henke et al. |
| 2010/0069752 | A1 | 3/2010 | Lewandowski et al. |
| 2010/0191144 | A1 | 7/2010 | Zoth et al. |
| 2010/0272299 | A1 | 10/2010 | Van Schuylenbergh et al. |
| 2011/0243789 | A1 | 10/2011 | Roberts |
| 2012/0232387 | A1 | 9/2012 | Miyachi |
| 2012/0289162 | A1 | 11/2012 | Hosoi et al. |
| 2013/0303941 | A1 | 11/2013 | Porges et al. |
| 2013/0317361 | A1 | 11/2013 | Tabaru et al. |
| 2014/0323862 | A1 | 10/2014 | Silverman et al. |
| 2015/0110333 | A1 | 4/2015 | Norris |
| 2015/0133746 | A1 | 5/2015 | Oyadiran et al. |
| 2016/0128558 | A1 | 5/2016 | Larin et al. |
| 2016/0242650 | A1 | 8/2016 | Chen et al. |
| 2016/0367143 | A1 | 12/2016 | Catheline et al. |
| 2017/0014053 | A1 | 1/2017 | Moehring et al. |
| 2017/0055946 | A1 | 3/2017 | Fujii |
| 2017/0290503 | A1 | 10/2017 | Larin et al. |
| 2020/0187899 | A1 | 6/2020 | Moehring et al. |
| 2020/0245975 | A1 | 8/2020 | Moehring et al. |

FOREIGN PATENT DOCUMENTS

| | | | |
|---|---|---|---|
| JP | H0450750 | A | 2/1992 |
| JP | H05115481 | A | 5/1993 |
| JP | H07111987 | A | 5/1995 |
| JP | 2001517105 | A | 10/2001 |
| JP | 2004069668 | A | 3/2004 |
| JP | 2004108794 | A | 4/2004 |
| JP | 2011525619 | A | 9/2011 |
| KR | 20030055430 | A | 7/2003 |
| KR | 20090128613 | A | 12/2009 |
| KR | 20100130765 | A | 12/2010 |
| KR | 101009779 | B1 | 1/2011 |
| WO | WO-9639924 | A1 | 12/1996 |
| WO | WO-2007061408 | A1 | 5/2007 |
| WO | WO-2009151216 | A2 | 12/2009 |
| WO | WO-2011127063 | A1 | 10/2011 |
| WO | WO-2016052817 | A1 | 4/2016 |
| WO | WO-2017011035 | A1 | 1/2017 |
| WO | WO-2020013868 | A1 | 1/2020 |

OTHER PUBLICATIONS

EP16824814.4 Extended European Search Report dated Feb. 4, 2019.
EP18925875.9 Extended Search Report dated Feb. 18, 2022.
Final Office action dated Mar. 21, 2019 for U.S. Appl. No. 15/173,615.
International Search Report for PCT/US2018/042138—Oct. 22, 2018.
Office Action date Jul. 26, 2018 for U.S. Appl. No. 15/173,615.
Office action dated Jul. 18, 2019 for U.S. Appl. No. 15/173,615.
PCT/US16/19432 International Search Report dated May 11, 2016.
U.S. Appl. No. 15/173,615 Notice of Allowance dated Feb. 6, 2020.
U.S. Appl. No. 14/797,181 Notice of Allowance dated Jan. 23, 2020.
U.S. Appl. No. 14/797,181 Office Action dated Feb. 25, 2019.
U.S. Appl. No. 14/797,181 Office Action dated Oct. 18, 2019.
U.S. Appl. No. 16/739,557 Notice of Allowance dated Dec. 20, 2022.
U.S. Appl. No. 16/739,557 Office Action dated Apr. 28, 2022.
U.S. Appl. No. 16/788,379 Corrected Notice of Allowability dated Feb. 13, 2023.
U.S. Appl. No. 16/788,379 Notice of Allowance dated Jan. 13, 2023.
U.S. Appl. No. 16/788,379 Office Action dated Mar. 31, 2022.
U.S. Appl. No. 18/186,049 Notice of Allowance dated Jul. 31, 2024.
U.S. Appl. No. 18/186,049 Office Action dated Oct. 17, 2023.
U.S. Appl. No. 18/298,136 Notice of Allowance dated Aug. 16, 2024.
U.S. Appl. No. 18/298,136 Office Action dated Jan. 19, 2024.

Baseband Signal Processor

100

200

RF Signal Processor

Input signal phase

Sampled Displacement w/phase wrap

Unwrapped phase estimate

CW Baseband Signal Processor

Waveform Plots (CW baseband processor)

APPARATUS AND METHOD FOR CHARACTERIZATION OF A DUCTILE MEMBRANE, SURFACE AND SUB-SURFACE PROPERTIES

CROSS-REFERENCE

This application is a continuation of U.S. patent application Ser. No. 18/298,136, filed Apr. 10, 2023, which is a continuation of U.S. patent application Ser. No. 16/788,379 filed Feb. 12, 2020, now U.S. Pat. No. 11,660,074, issued May 30, 2023, which is a continuation of U.S. patent application Ser. No. 15/173,615, filed Jun. 4, 2016, now U.S. Pat. No. 10,675,001, issued Jun. 9, 2020, all of which are incorporated herein by reference in their entirety.

FIELD OF THE INVENTION

The present invention relates to a device for characterization of any of a ductile membrane, a surface, or sub-surface material properties. In particular, the invention relates to the non-contact characterization of a ductile membrane, surface or sub-surface regions by stimulating the surface or membrane using a low frequency excitation such as an audible excitation and measuring the displacement behavior with a comparatively higher frequency excitation such as ultrasound.

BACKGROUND OF THE INVENTION

The measurement of a ductile surface or membrane is traditionally done by external application of a force to develop an understanding of the reaction to the surface or membrane to the application of a force. For the case of an elastic surface or membrane behavior, an example characterization may be drawn to a spring constant over a short range of motion, or in the case of a displacement in one direction followed by a non-linear displacement in the opposite direction, for a lossy system, a hysteresis effect may also be observed. There are several conditions of interest associated with the relationship between the membrane and an adjacent fluid or gel. In one condition, the membrane ductility dominates the measurement, and the effect of materials adjacent to the membrane such as air, fluid, or gel have no effect on the measurement, as the membrane characteristic dominates the measurement. In another condition, the membrane provides an interface and challenge surface for a surface stimulation, and the characteristics of the fluid or gel adjacent to the membrane are measured using the membrane, which otherwise does not change the characteristics being measured, as the membrane is closely coupled to the surface and underlying fluid such that displacements to the underlying fluid may be made through the surface or membrane without changing the characteristics to be measured. Such characterizations are widely performed using mechanical (stirring paddles) or other means in the food industry to measure the stiffness or other mechanical properties of various liquid or semi-solid food items, such as those with curing or culture times. For example, in the prior art of food science, it is desired to know when yogurt has reached a particular culture level by its mechanical properties, whereas the bacterial growth interval may be determined from prior batches and a fixed interval used. Similarly, the ripeness of a fruit or vegetable may be determined by its surface softness, elasticity, or other mechanical property, which may be performed by the application of a small force sufficient to produce measurable deflection or which causes surface or shear waves across the surface of the fruit or vegetable and measuring the minute surface or sub-surface deflections in response to that surface force.

Accordingly, it is desired to measure the mechanical properties of food items using non-contact methods of measurement applied to the surface of the item to be characterized.

In the medical field, it may be desirable to measure the elasticity of a skin surface, a movable membrane, or organ surface. In one example, the eye globe may be measured by using a contact or optical method, to determine the deflection upon application of an air puff. In the prior art, the optical reflectivity characteristics of the eye may be measured as a deflection versus applied force. However, the optical interface of the eye and the various underlying structures may have resolution of motion limitations which are the consequence of the optical measurement system characterizing an optically transparent structure, where the intended target (such as the cornea) and surrounding structures (such as the ocular lens and vitreous fluid) have similar optical properties and are therefore difficult to resolve from each other. It is desired to use remote sensing and remote interrogation, such as through air, to measure the elasticity of the surface of an eye or other organ.

Ultrasound measurements are typically performed using a liquid medium as a coupling fluid, such that the ultrasound energy propagates from the transducer through the fluid as traveling acoustic waves, creating reflected ultrasound energy arising from target interfaces which have differences in acoustic index of refraction according to the transmission impedance mismatch between the coupling fluid and the target. The use of ultrasound has not been possible for non-contact displacement measurements resolving distances on the order of millimeter (mm) and sub-mm distance ranges because of the traditional requirement for coupling fluids between the transducer and target.

A method for the non-contact surface characterization of a surface through remote sensing of displacement in combination with the application of a surface stimulus is desired. It is further desired to use air as the medium for stimulation and measurement, without direct contact to the surface or membrane by either the stimulus or measurement device.

OBJECTS OF THE INVENTION

A first object of the invention is an apparatus and method for the generation of a pulsatile mechanical stimulation for application to a surface or membrane, the mechanical stimulation combined with an ultrasonic measurement of the response of a surface or membrane to the stimulation by examination of a reflected ultrasound signal, and the characterization of the reflected response to determine mechanical properties of the surface or membrane.

A second object of the invention is the measurement of surface, sub-surface, or membrane ductility and elasticity by examination of an ultrasound signal which has reflected from the surface, sub-surface, or membrane.

A third object of the invention is an apparatus and method for the application of a force to a food item, the force generating a surface or membrane deflection with a temporal response, including a shear wave or surface wave, the surface or membrane deflection characterized by a phase or amplitude change in an ultrasound signal which has reflected from the surface or membrane.

A fourth object of the invention is the characterization of a substantially homogeneous fluid for elasticity or viscosity by application of a non-contact displacement force and characterization of the response to the non-contact displacement force by measuring the phase and amplitude of reflected ultrasound from transmitted ultrasound applied to the surface of the fluid.

A fifth object of the invention is an apparatus and method for the measurement of an elasticity of an animal or human organ, whereby an air puff is applied to the organ, such as a human eye to perform tonometry, and the response of the organ is measured, where the air puff response of the organ during the response time of the relaxation from air puff results in a characteristic phase change of the reflected ultrasound energy compared to the phase of the applied ultrasound energy over a continuous wave (CW) ultrasound interrogation or a series of pulsed ultrasound interrogations.

SUMMARY OF THE INVENTION

The present invention may utilize an ultrasound transducer, such as a capacitive micro-machined ultrasound transducer (cMUT), which provides a diaphragm structure with a thin diaphragm which provides a good impedance match to gaseous media for propagation of ultrasonic energy through air from the displacement of the diaphragm. Accordingly, the cMUT is suitable for coupling through air, and is suitable for duplication in a planar 2D hex packing array, such as on a substrate, for generation of a planar wave of desired spatial characteristic and lateral extent. In one example embodiment, a material which is optionally on the far surface of a membrane can be characterized by the application of a pulsatile challenge displacement force such as by an air puff, where an ultrasound transducer measures the dynamic displacement characteristics of the membrane or surface. In one example, the membrane transparently provides a physical barrier to the material to be characterized, and so does not significantly change the properties of the material as seen by the ultrasound transducer. The ultrasound transducer sends and receives ultrasound energy through a medium such as air to the surface or membrane to be characterized, the ultrasound transducer operative during an interval when a comparatively low frequency excitation source is coupled to the surface or membrane. The low frequency excitation source generates a subtle movement of the surface or membrane during an interval coincident with an ultrasound transmitter delivering acoustic wave ultrasound energy to the surface or membrane either in CW form or in pulsed form. A receiver for ultrasound reflected from the surface or membrane measures displacement of the surface or membrane as a phase change in the received signal when compared to the transmit frequency, thereby indicating a temporal displacement of the surface or membrane. An analysis of the temporal displacement of the surface or membrane, as measured by the phase shifts of the reflected ultrasound in response to the pneumatic excitation coupled to the surface or membrane, in combination with comparison to the temporal displacement or from templates or metrics associated with the delay in and amplitude of response between the excitation stimulus to and ultrasound response from the surface or membrane, is used to determine the mechanical characteristics of the surface or membrane. The mechanical characteristics measured may include ductility, elasticity, or hardness. In this manner, a non-contact measurement of the mechanical properties the fluid below the surface or membrane may be determined.

Aspects of the present disclosure provide a non-contact characterization system. A non-contact characterization system may comprise an excitation generator generating a non-contact displacement force directed to a remote object to be characterized. A non-contact characterization system may comprise an ultrasound transducer directing ultrasonic energy to a remote object; a transmit waveform generator coupled to the ultrasound transducer. A non-contact characterization system may comprise a receive signal processor coupled to the ultrasound transducer, and receiving ultrasound energy reflected from a remote object, the receive signal processor comparing the received ultrasound signal amplitude or phase to a transmit signal formed by the transmit waveform generator, the receive signal processor thereby forming an estimate of remote object displacement in response to the non-contact displacement force.

The excitation generator may form a puff of air directed to a remote object. The puff of air may contain a non-oxidizing gas. The non-oxidizing gas may be at least one of: nitrogen, argon, CO2, helium. The ultrasound transducer may be a capacitive micromachined ultrasonic transducer (cMUT). The transmit signal generator may be either a continuous wave (CW) or pulsed signal generator operative at a fundamental or harmonic frequency of the ultrasound transducer transmit frequency. The receive signal processor may perform baseband demodulation of a received signal and form an estimate of displacement from a series of phase estimate, each phase estimate determined from a phase displacement of the received signal compared to the transmitted signal. The series of phase estimates may form an elasticity metric.

Another aspect of the present disclosure provides a method for non-contact measurement of an elastic surface. A non-contact force event may be provided. The excitation generator may provide a non-contact force to a surface or a volume of material adjacent to the surface to be characterized. A series of displacement measurements may be formed for each applied excitation generator non-contact force event. Ultrasound energy may be directed from a transducer to a surface or adjacent volume of material to be characterized. The transducer may receive reflected ultrasound energy from the surface or volume to be characterized. The phase of the transmitted ultrasound energy may be compared to the received ultrasound energy to form a displacement estimate. A plurality of said displacement measurements may be used to estimate an elasticity or a viscosity.

The excitation generator non-contact force may be a puff of air released from a nozzle directed at a surface on or of a material to be characterized. The puff of air may be an inert gas including at least one of: Nitrogen, Argon, CO2 or Helium.

The transducer may be at least one of a cMUT or piezoelectric transducer. The directing ultrasound energy may be a continuous wave (CW) ultrasound energy on a transmit transducer. The comparing the phase of the transmitted ultrasound energy to the received ultrasound energy may form a phase displacement which may be converted to a non-contact displacement of a material to be measured. The estimate of elasticity or viscosity may be performed by comparing a series of measured phase displacements to a template series of measurements. The estimate of elasticity or viscosity may be performed by examination of a rise time or a fall time of a displacement compared to the rise time or fall time of said excitation source.

The excitation may be a step or impulse pressure. The estimate of elasticity or viscosity may be performed by examination of a ringdown characteristic. The ringdown characteristic may be at least one of an exponential decay time or a ring cycle interval or frequency. The excitation may propagate to the surface or the volume to be characterized as a surface wave, a shear wave, or a combination of surface wave and shear wave.

The surface or volume to be characterized may include a membrane over a fluid. The surface or volume to be characterized may include a fluid having an elasticity or viscosity. The surface or volume to be characterized may include an animal or human.

Another aspect of the present disclosure may provide a non-contact material characterization system. The non-contact material characterization system may comprise an excitation generator. The excitation generator may be configured to generate a non-contact displacement force directed to an elastic surface or to a volume of material adjacent to the elastic surface. The non-contact material characterization system may comprise an ultrasound transducer. The ultrasound transducer may be configured to direct a transmit signal to the surface or to the volume. The ultrasound transducer may be configured to receive a reflected Doppler ultrasound signal from the surface or the volume. The non-contact material characterization system may comprise a processor coupled to the ultrasound transducer. The processor may be configured to determine a displacement of the surface or the volume in response to the non-contact displacement force and the reflected Doppler ultrasound signal.

The processor may be configured to determine the displacement by comparing at least one of an amplitude or a phase of the reflected Doppler ultrasound signal to at least one of an amplitude or a phase of the transmit signal. The non-contact displacement force generated by the excitation generator comprises a puff of air. The excitation generator may be configured to generate the non-contact displacement force with a frequency of at least 20 Hz. The non-contact displacement force generated by the excitation generator comprises an impulse excitation. The ultrasound transducer may comprise a capacitive micromachined ultrasonic transducer (cMUT) or a piezoelectric transducer.

The non-contact material characterization system may comprise a waveform generator coupled to the ultrasound transducer. The waveform generator may comprise either a continuous wave (CW) or a pulsed signal generator. The waveform generator may be operative at a fundamental or a harmonic of a frequency of the transmit signal.

The processor may be configured to determine the displacement by performing a series of comparisons of the phase of the reflected Doppler signal to the phase of the transmit signal. The processor is further configured to perform baseband demodulation of the reflected Doppler signal. The processor may be configured to determine at least one of an elasticity or a viscosity of the elastic surface or volume based on the series of phase estimates. The processor may be configured to determine at least one of an elasticity or a viscosity of the elastic surface or volume based on the determined displacement.

Another aspect of the present disclosure provides a method for measurement of an elastic surface. A non-contact displacement force may be provided to the elastic surface or to a volume of material adjacent to the elastic surface (step (a)). Ultrasound energy may be transmitted from a transducer to the surface or a volume adjacent to the elastic surface (step (b)). Reflected Doppler ultrasound signal may be received at the transducer (step (c)). At least one of an amplitude or a phase of the transmitted ultrasound energy may be compared to at least one of an amplitude or a phase of the reflected Doppler ultrasound signal to form a displacement measurement (step (d)). An elasticity or a viscosity may be calculated from the displacement measurement in response to the non-contact displacement force.

Providing the non-contact force to the elastic surface or to the volume of material adjacent to the elastic surface may comprise directing a puff of air to the elastic surface or to the volume of material adjacent to the elastic surface. The non-contact displacement force may comprise an impulse excitation. The transducer may comprise a capacitive micromachined ultrasonic transducer (cMUT) or a piezoelectric transducer. Transmitting the ultrasound energy may comprise transmitting continuous wave (CW) ultrasound energy.

The method may comprise repeating steps (a) to (d) to perform a series of displacement measurements, and comparing the series of displacement measurements to a template series of displacement measurements of a known material. Calculating the elasticity or the viscosity may comprise comparing a rise time or a fall time of the displacement measurement to a rise time or fall time of the non-contact displacement force.

Providing the non-contact force may comprise providing a step or impulse pressure. Calculating the elasticity or the viscosity may comprise analyzing a ringdown characteristic of the reflected Doppler ultrasound signal. The ringdown characteristic may comprise at least one of an exponential decay time, a ring cycle interval, or a ring cycle frequency.

The non-contact displacement force may propagate to the surface or the volume as at least one of a surface wave or a shear wave. The surface or the volume may comprise a membrane over a fluid. The elastic surface may comprise tissue of an animal or a human. The elastic surface may comprise a solid or semi-solid food item. The non-contact displacement force may be provided at a frequency of at least 20 Hz.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4C-1 shows a plot of a sinusoidal surface or membrane displacement generating more than +/−180° of phase shift.

FIG. 4C-2 shows the acquired data with phase wrapped from the large phase shifts of FIG. 4C-1.

FIG. 4C-3 shows a plot of an unwrapped phase estimate from FIG. 4C-2.

DETAILED DESCRIPTION OF THE INVENTION

Figure 1:
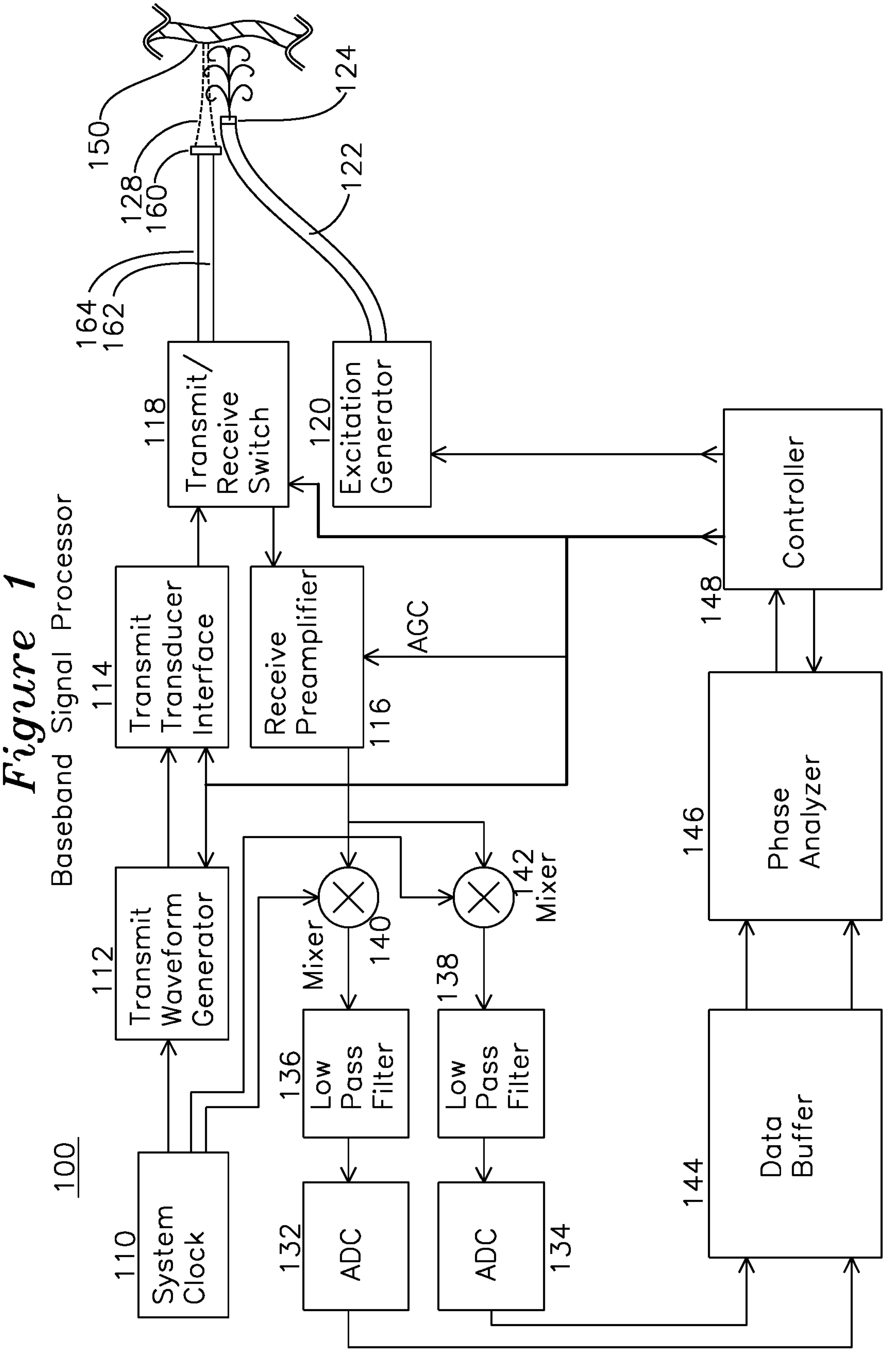
FIG. 1 is a block diagram of a signal processor system for estimating the characteristics of a surface or membrane.

FIG. 1 shows a signal processor for an example embodiment of a non-contact, gas coupled surface, sub-surface, or membrane characterization system. A surface 150 may be a membrane or a compressible surface with elastic characteristics. The surface 150 is interrogated by an ultrasound beam 128 from an ultrasound transducer 160 which is optionally mounted adjacent to a source of applied non-contact force, such as a gaseous puff such as an air puff, which is conveyed through hose 122 to nozzle 124, or other means for providing a non-contact pressure stimulus to a membrane or surface such that the response of the membrane or surface to the non-contact force can be observed. The nozzle 124 may be coupled to an interior volume which provides for coupling of dynamic pressures from surface excitation generator 120 through hose 122 to the surface 150 where the air pressures result in displacement of the surface 150. This displacement can also be the result of a pressure differential, such that one side of a membrane or surface is momentarily greater or lower than the other side, and the surface or membrane response characterized after the pressure differential is in steady state. The excitation generator 120 may generate static or dynamic pressure variations which are coupled to the surface 150. As above, the excitation generator 120 may produce any suitable static or dynamic pressure modulation for displacement of the surface, including a sub-audio frequency below 20 Hz, an audio frequency from 20 Hz to 20 KHz, or a super-audio frequency above 20 KHz. The nature of the pressure excitation generated by the excitation generator may be an impulsive step or delta (impulse) generation, a sinusoidal pressure excitation, a square wave excitation, or any combination of these, and the excitation may be a gated burst or continuous. The pressure excitation may be provided with or without a static positive or negative pressure bias. Pressure nozzle 124 also has an adjacent ultrasound transducer 160 with electrical leads 162 and 164 coupled to transmit receive switch 118. Ultrasound transducer 160 generates ultrasound beam 128 which is directed to a central region of the surface 150. A controller 148 generates a variety of control signals which are distributed through the signal processor 100. A system reference clock 110 may be derived from a temporally stable clock source, and the reference clock 110 may also be used for demodulation of the received signal. System reference clock 110 is coupled to a transmit waveform generator 112 which generates a pulse train at or near the center frequency of transducer 160, transmit transducer interface 114 performs voltage level shifting and any required amplification before coupling to the transmit/receive switch 118, which couples the waveforms from transmit interface 114 to the ultrasonic transducer 160 via leads 162 and 164. The ultrasound transducer 160 generates and directs the ultrasonic energy in beam 128 to the surface 150. Reflected energy from the surface 150 is coupled from the transducer 160 back through leads 162 and 164 to the transmit/receive switch 118, where it is directed to the receive preamplifier 116, which amplifies the signal level and isolates the signal using frequency filtering to remove out-of-band frequency components, and optionally provides automatic gain control through a gain control input from controller 148. The output of the receive preamplifier 116 is applied to quadrature mixers 140 and 142, where a quadrature clock from clock generator 110 at the ultrasound transmitting frequency generates a quadrature output comprising an I (in-phase) baseband channel and Q (quadrature, or 90 degrees separated) baseband channel, which are coupled to identical low pass filters 136 and 138, each of which has a respective analog to digital converter 132 and 134, the output of which is stored in data buffers 144, one data buffer for each I and Q channel. It is also possible to provide multi-gate samples over time, so that if the target moves out of the range of a particular gate, the system can adaptively use samples associated with the subsequent depth. For example, for a transducer center frequency of 2 MHZ, ultrasound propagation velocity of 0.33 mm/μs c/f=170 ns, an 8 cycle burst at 2 mhz would be 4 μs, ct/2=⅓ of 2 μs=600 u. If speculum were to adjust by 1 mm, signal would go away from where TM shows up as a peak signal, if movement of 0.5 mm of TM, that is only 2× desired perturbation range, could take to the edge of sample volume. multiple adjacent sample volumes should be included to, use greatest reflection amplitude of the various samples using I&Q of adjacent signal samples. The gain control applied to preamplifier 116 is set to place the I and Q signals in an optimum converter range for the A/D converters 132 and 134. When the received signal is mixed with the reference clock in this manner, each transmit pulse generates a single phase value per range gate sample at a particular depth, and over a series of transmit events this sequence of phase differences is used by the phase and amplitude analyzer 146 to estimate the temporal displacement of surface 150. In one embodiment of the invention, the transmit clock coupled to the transducer during the transmit interval is derived from system clock 110, which is substantially at the center frequency of the transducer. In an example embodiment where the phase and amplitude analyzer 146 examines primarily the phase of the returned signal, the system clock, at the transmit rate, supplies synchronous clocking to quadrature mixers 140 and 142 during the receive interval to compare the receive signal phase to the system clock (at the original transmit frequency) to generate a phase difference between the transmitted pulse and the reflected pulse. This phase value may be compared over one or more cycles of the receive signal to establish an average phase value for that particular receive interval, and then each phase value from each receive interval is assembled to provide a continuous series of discrete estimates of surface 150 displacement, based on the wavelength of the acoustic wave and the phase value measured. In another example embodiment, the phase and/or amplitude analyzer 146 may operate on the amplitude of the received signal, which may be analyzed to provide information about the quality of the phase estimate made from the data (such as from signal to noise metrics), or the amplitude of the signal may be analyzed to provide a metric such as db/MHz-cm falloff, or the amplitude profile may provide an elasticity metric which indicates the elasticity or other surface characteristic based on the reflection of ultrasound energy from the surface, in response to the momentary pressure perturbation provided by the excitation generator. In general, the elasticity metric is any phase or amplitude derived metric from the data presented to the amplitude and phase analyzer 146 which provides a measurement of surface elasticity, where the mobility is preferentially associated with the elasticity of the surface 150. Controller 148 which generates the excitation 122 also reads the output of phase and amplitude analyzer 146 over the duration of excitation generator 120 activity, and optionally the amplitude of the reflected signal, to derive a temporal response of the surface 150 to the pneumatic excitation provided through coupling tip 124. The pneumatic excitation may be any sub-audio, audio, or super-audio frequency or pulse as previously described.

Figure 2:
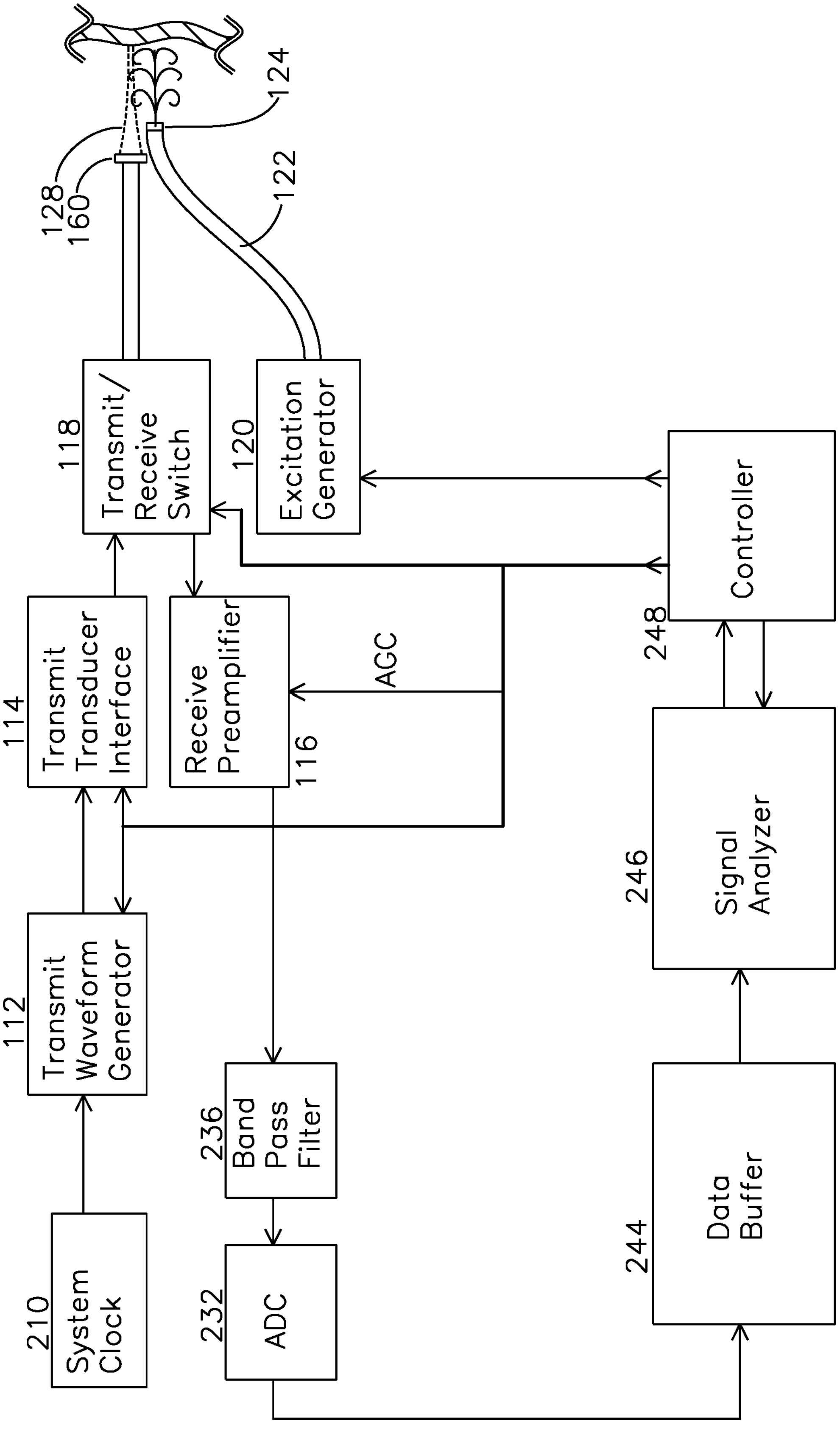
FIG. 2 is a block diagram as in FIG. 1 where the signal processor operates directly on received ultrasound echoes.

FIG. 2 shows an alternate embodiment of the signal processor of FIG. 1, where the signal processor is performing direct sampling of the RF signal from the transducer, rather than using quadrature mixing to baseband of the RF signal. System clock 210 generates the transmit clock, which is coupled to transmit waveform generator 112. The operation of transmit waveform generator 112, transmit transducer interface 114, transmit receive switch 118, receive preamplifier 116, surface excitation source 120 and transducer 160 are as previously described for FIG. 1. The receive preamplifier 116 may be gain controllable, as before, with the gain determined by controller 248 to place the RF signal in optimum A/D converter 232 range. The output of the receive preamplifier 116 is directed to a band pass filter 236 for reduction of the noise bandwidth applied to the ADC 232, which samples at the Nyquist rate of at least 2× faster than the applied signal. For the case of a 1.5 MHz transducer 160, the Nyquist sampling rate is at least 3 MHz plus the skirt falloff associated with the bandwidth of the transducer 160, known in the art of signal sampling as the Nyquist sampling criteria. The single channel output of the ADC 232 is applied to a data buffer 244, and a signal analyzer 246 examines phase shifts in the buffered signal to determine phase changes of the RF signal to discern movement of the surface. The sequence of phase measurements used to form the phase measurement may be a series of measurements which are inverse-time weighted to increase the effect of recently acquired measurements, or they may be uniformly weighted over a window of phase samples. The use of a weighting coefficients applied to the stream of measurements over a window may provide favorable noise rejection characteristics, and weighting may be chosen to favor signals in the excitation source bandwidth to filter and reduce the effect of noise which is outside the excitation source bandwidth.

Figure 3:
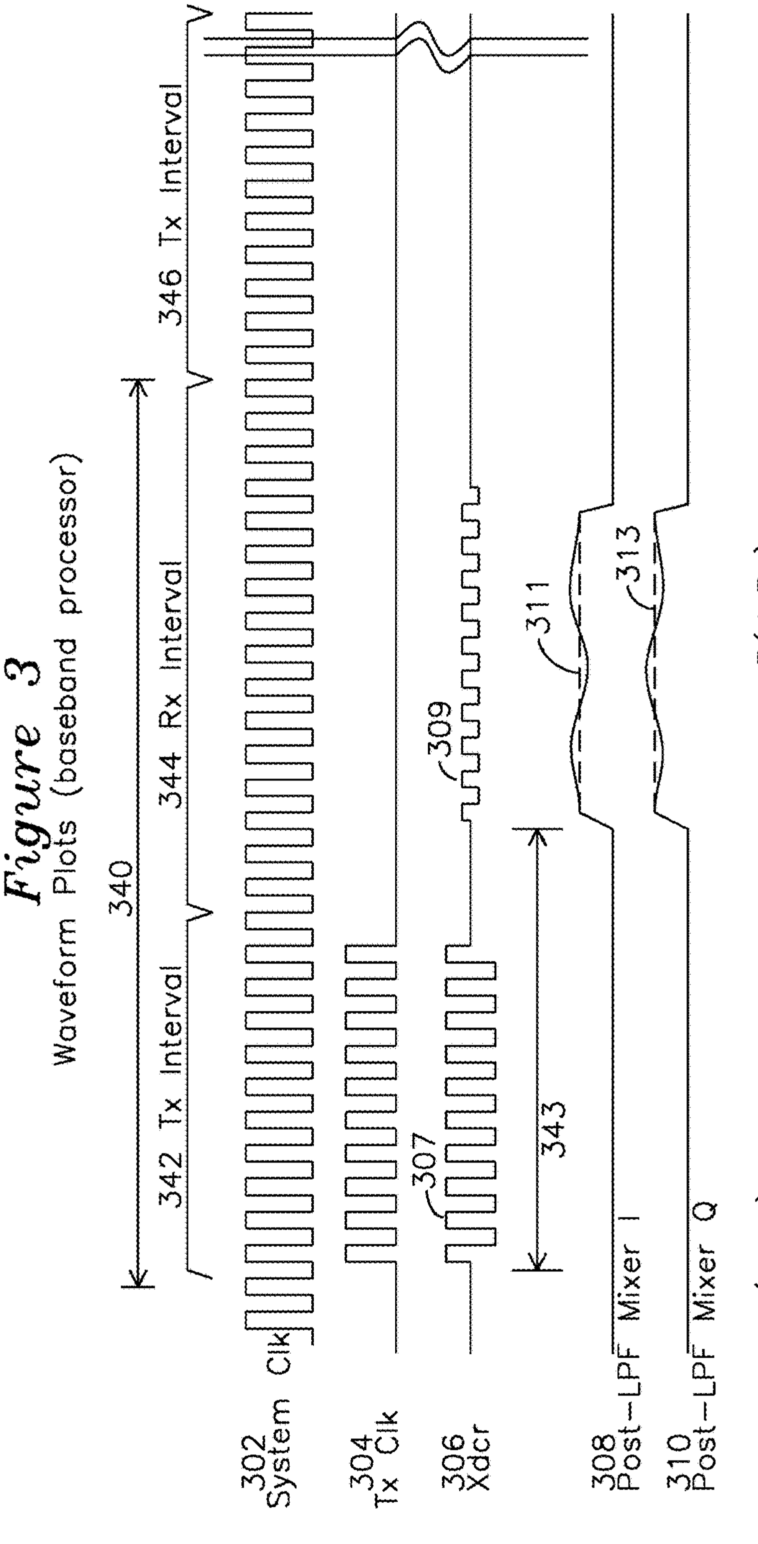
FIG. 3 shows waveforms for the system of FIG. 1.

FIG. 3 shows example operation of the ultrasound processor of FIG. 1. In a pulsed RF mode, transmit/receive events provide an estimate of the surface position as a series of phase values during a series of repeated interrogation intervals 340, each of which provides a single phase value. System clock waveform 302 operates continuously, and is furnished by system clock generator 110 of FIG. 1. The duration of the event interval 340 is determined by the time-of-flight from the transducer 160 to the surface 130 and back to the transducer 160 of FIG. 1. The propagation velocity of ultrasound in air is 330 m/s (0.33 mm/μs). Accordingly, for a 1.5 MHz transducer, the resultant wavelength of this traveling wave in air is 0.22 mm. The total time of flight for an ultrasound signal 10 mm each direction is then 60 μs, so duration 340 may be no less than 60 μs in this case. This time of flight interval for a transmit pulse to return as a receive signal after reflection is shown as interval 343 in FIG. 3. The time of flight provides an upper limit to the pulse repetition frequency (PRF) corresponding to the sum of the transmit interval and receive interval. For this example, the transducer with a 1.5 MHz center frequency will have a 220 u wavelength traveling in air. A displacement of the surface will result in a shortened path from the transducer to the surface, and the reflected signal from the surface back to the transducer will return with a phase shift. Accordingly, the phase and amplitude analyzer observing a phase offset of 180 degrees between transmit clock and received signal compared to a datum phase offset will correspond to a 55 μm displacement of the surface. A transmit interval 342 for the transmission of a longer pulse train provides improved signal to noise ratio of the receive signal phase and also extends the return time of flight by the duration 342 of the transmit pulse stream, at the expense of decreased axial resolution, which may be desirable for the case of a discrete moving target such as the surface. For a 10 cycle stream at 1.5 MHz, transmit interval 342 is 6.6 μs, and for the reflected signal from a previous transmit burst to not interfere with the new transmit burst, the maximum interval 340 is 66.6 μs, which implies a pulse repetition frequency (PRF) of 15 KHz or less. In a limiting case where the surface is 30 μs one way time-of-flight distant, and most of the signal energy reflection is at the air/fluid interface of a surface with fluid behind it, and with minimal signal energy reflected from structures beyond the surface, the shortest possible repetition cycle time is 30 μs (maximum transmit burst length)+30 μs (outgoing time of flight)+30 μs (return time of flight). In this idealized scenario, the transducer starts transmitting at t=0 of the repetition cycle. At t=30 μs, the first cycle of transmit energy reaches the surface at the same time the transducer is finishing sending the last of the transmit burst. At t=60 μs, the first reflected cycle is reaching the transducer and the last cycle of the burst is reflecting from the surface, and at t=90 μs, the last cycle of the burst has reached the transducer. In an actual ultrasound system, the PRF will be much lower to account for the required attenuation of multi-path reflection energy which will mix with the surface reflections. In a CW system, separate transmit and receive transducers are used and multipath considerations can be ignored when the surface to be measured has signal energy which dominates the Doppler signal energy which is returned. It may be preferable for the system to operate in CW mode in some circumstances, and in pulsed mode in others, depending on the nature of the reflected signal energy. For pulsed mode, several parametric changes are available to improve SNR, including the use of shorter or longer bursts of transmit RF energy (307 of FIG. 3) which match the spatial extent of the diaphragm or fluid which is responding coherently to the excitation, such as by moving in a common direction, as a stronger reflected signal with better SNR is provided when the sample volume which is returning acoustic energy is in motion in the same direction. Alternatively, it is possible to use a short transmit burst 307 with spatial extent which matches the regions of diaphragm or fluid which are moving in the same direction, and to successively range gate or sample each region of the reflected signal separately to distinguish movement or displacement of one region from movement or displacement of another region, thereby treating each reflection region separately. This may also provide advantage where a membrane or surface moves into range of one sampled region and out of range of another sampled region (such as the spatial extent represented by waveforms 311/313 of FIG. 3). It is alternatively possible to provide many cycles of transmit energy to improve the phase accuracy of each measurement, particularly where a clear surface reflection boundary is present and most of the signal energy is reflected from the surface. The combined transmit interval and receive interval which determine the PRF may be in the repetition period range of 50 μs to 1 ms or more. As multi-path reflections may occur, it may be preferable to reduce the maximum PRF to reduce the effect of ultrasonic reflections from transmit events earlier than the current interval 340, for example. For an ultrasound propagation velocity of 0.33 mm/μs, when the separation from the transducer to surface is 15 mm, the round trip ultrasound path requires ~90 μs, and if the separation distance from transducer to surface is 20 mm, the round trip path requires ~120 μs. As an example, for the 20 mm separation distance, a transmit burst length of 15 cycles at 1.5 MHz would add an additional 10 μs, and adding 20 μs of settling time for multipath reflections would result in an interval 340 of 150 μs, corresponding to a PRF of ~6.67 KHz. Transducer waveform 306 shows the transmit waveform 307 which includes bias and amplitude corrections during the transmit interval 342, and a reduced amplitude receive signal 309 from the surface. The received signal 309 also includes the effects of surface displacement in the form of a phase change from the system clock, which must be subtracted from any static phase value which may be present. Mixer I and Q outputs, after low pass filtering, are shown as waveforms 308 and 310, respectively. Each 66 μs cycle provides a single phase estimate value, which may be considered in polar coordinates using the I and Q outputs. This may be done using a range gate select a time of flight interval corresponding to the region containing a reflection from the surface to obtain each sample indicating the instantaneous phase of the surface for a particular sample from a transmit event. Each of the acquired values within an RX interval 344 is averaged or temporally filtered over the temporal region corresponding to the surface reflected response to reach an average phase estimate shown as 311 and 313, respectively, for I and Q waveforms 308 and 310. A series of such phase estimates are saved, each of these estimates spanning an extent of the Rx interval 344 and which extent corresponds to a reflection from a particular depth. Across multiple data acquisition Rx intervals 344, the samples of IQ are concatenated to construct a time series describing surface or sub-surface motion, since phase change over time is attributed to change in distance from the transducer. A succession of these sampled values are collected and compared against a surface excitation waveform which is used to form a characterization of the surface for a particular excitation waveform.

Figure 4A:
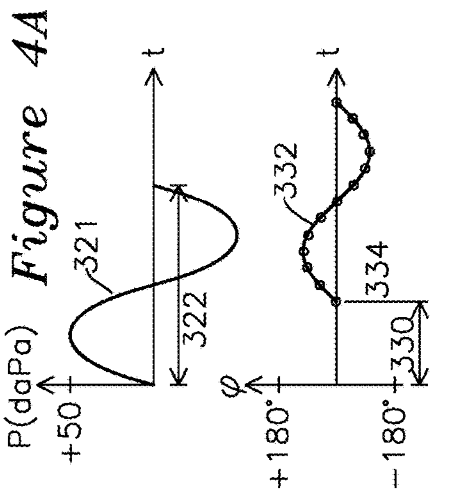
FIG. 4A shows a plot for a sinusoidal excitation applied to deformable surface or membrane with a reflected response signal having a phase delay and amplitude level.

FIG. 4A shows an example sinusoidal excitation applied to a surface, such as a sinusoidal waveform 321 applied using a voice coil diaphragm displacing a volume sufficient to modulate a localized region of the membrane or surface pressure by 100 daPa (dekapascals) p-p. Sub-sonic frequencies (<20 Hz) may require sealing the localized region around the excitation surface, whereas audio frequencies (20 Hz-20 kHz) and super-audio frequencies (>20 kHz) may be sufficiently propagated as audio waves without sealing the surface region. The sinusoidal pressure excitation 321 results in a modulation of the surface displacement, which is shown as phase plot 332, as the modulation in surface position corresponds to a change in the phase of the return signal. Each discrete circle of waveform 332 represents a sample point such as a polar conversion of average values for I 311 and Q 313. In one example embodiment of the invention, a series of sinusoidal modulation excitation 321 frequencies are applied, each with a different period 322, and the delay in response 330 and peak phase amplitude are used in combination to estimate the ductility of elasticity, or other surface or bulk fluid property. Since each 360 degree phase change of the 1.5 MHz transmit pulse corresponds to lambda/2=0.11 mm, a phase change of +/−180 degrees total as shown in plot 332 would correspond to 011 mm peak to peak displacement of the surface. By applying a series of audio and sub-audio tones with various cycle times 322 and measuring the phase response 330 as shown in plot 332, it is possible to estimate the characteristic such as viscosity or elasticity of the fluid behind the surface. For example, an exemplar elasticity metric measurement associated with the changed density or viscosity of the fluid could be an associated change in surface or membrane response time. In this manner, a frequency domain response of the surface may be made using a series of excitations 321 and measuring a series of surface responses 332.

Figure 4B:
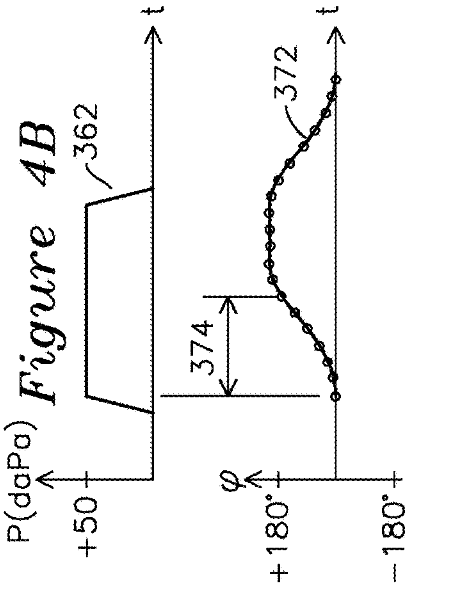
FIG. 4B shows a plot for a step excitation applied to a deformable surface or membrane, and a response to the step excitation having a phase delay and amplitude level.
Figures 1, 4C:
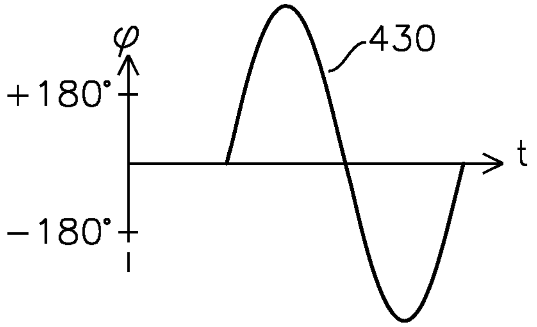
Figures 2, 4C:
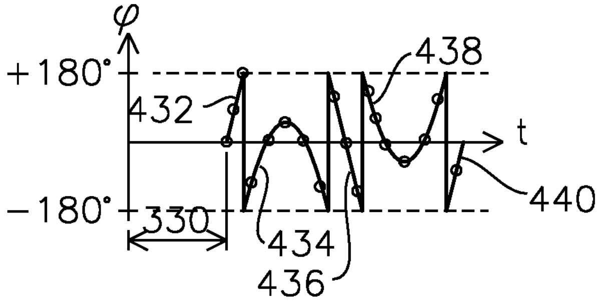
Figures 3, 4C:
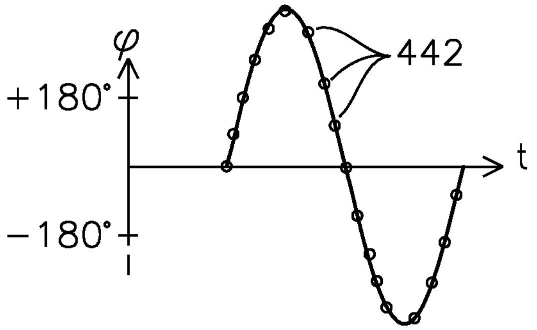

The series of FIGS. 4C-1, 4C-2, and 4C-3 show the effect of reconstructing surface displacements when the received signal phase exceeds λ/2 (180°, corresponding to a λ/4 surface displacement). FIG. 4C-1 shows a received signal 430 with displacement-associated phase excursions which exceed λ/2 (180°). Because phase excursions greater than 180° wrap to −180°, the series of samples of FIG. 4C-2 wrap and produce the series of samples shown, with samples of individual segments 432, 434, 436, 438, and 440. If a sufficiently high sample rate is used which exceeds the Nyquist sampling rate, it is possible to "unwrap" the samples as shown in FIG. 4C-3, to provide the original phase information. These techniques are well known in the prior art of Doppler signal reconstruction.

Whereas FIG. 4A shows a sinusoidal excitation which may be provided in a series of such excitations to generate a phase vs. frequency response plot of the surface displacement from the series of measurements, FIG. 4B shows a time domain step response equivalent of FIG. 4A, where a surface step pressure excitation 362 of 50 daPa peak is applied to the surface or membrane, which generates the phase response 372 of the return signal from the surface. It is similarly possible to characterize the surface response based on a time delay 374 and amplitude response (shown as 180 degrees) for phase response plot 372, corresponding to 1½ mm displacement. The phase unwrap techniques described in the series of FIG. 4C-1, 4C-2, 4C-3 may similarly be applied to the samples of waveform 372 of FIG. 4B to reconstruct phase shifts in excess of +/−180°.

The signal processing of FIG. 2 operates in a similar manner as was described for FIG. 3, however the reflection 306 observed by the transducer is directly sampled and compared with a reference clock to determine the phase changes associated with the surface movement, for example by multiplying the reference clock with the received signal over a receive signal averaging time, and integrating this value over the duration of the receive signal to estimate a phase value for one receive interval. In a similar manner, this will result in the generation of response waveform 332 from excitation source 321 interacting with the surface, as described for FIG. 4A, or response waveform 372 from excitation source 362 interacting with the surface. In one example embodiment of the invention where a surface interface is being characterized, the phase analyzer 146 or signal analyzer 246 is operative to detect the largest amplitude of the I or Q channel, or largest magnitude of vector generated by IQ, and associates the region of that large signal response as the surface to be characterized, subsequently sampling that region to form an estimate of phase offset from which displacement may be estimated.

Figure 5:
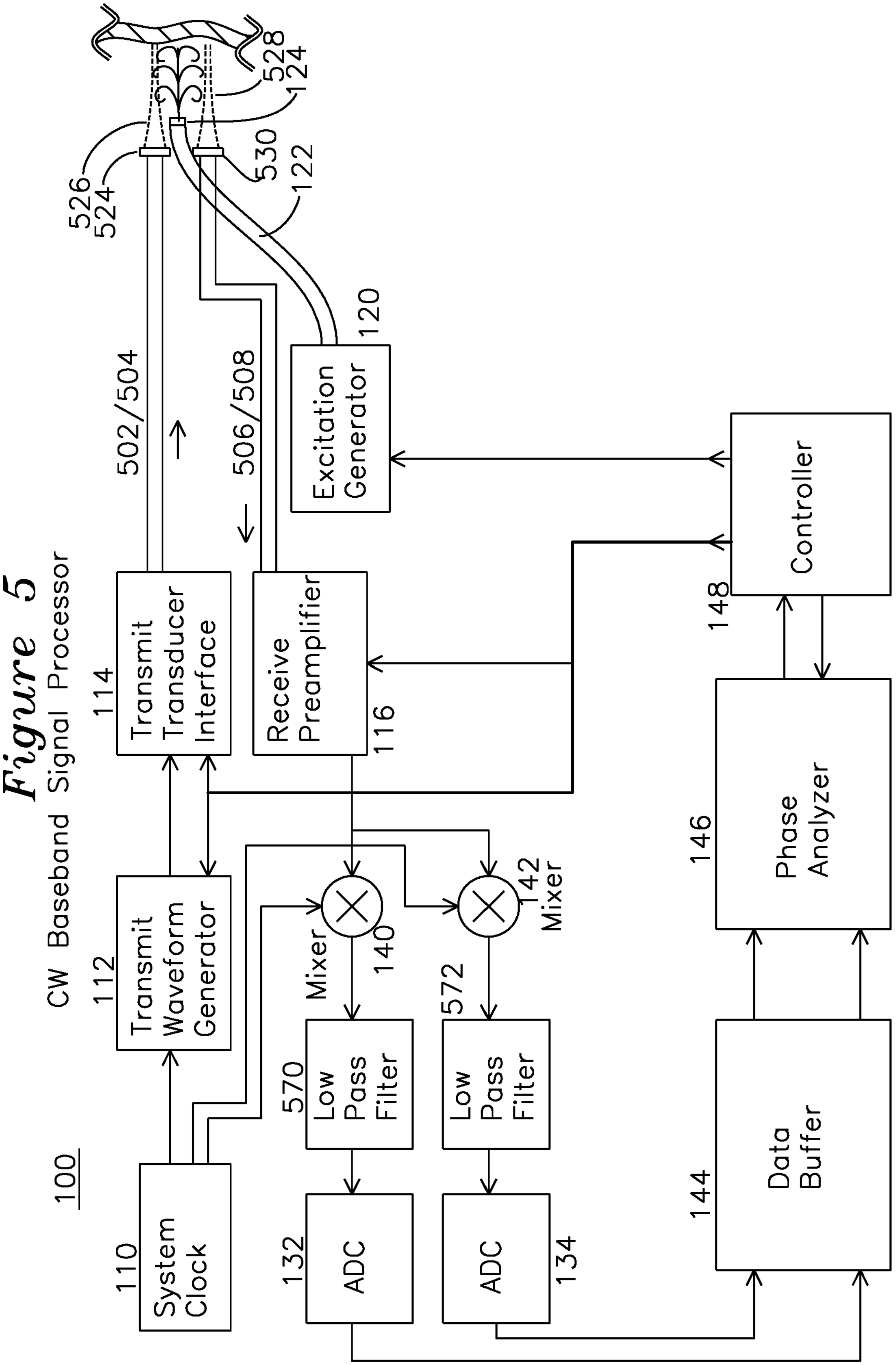
FIG. 5 shows a CW signal processor for continuous interrogation of a membrane or surface or membrane in response to an excitation generator.

FIG. 5 shows another embodiment of the invention for CW operation. The signal processor of FIG. 5 operates as in FIG. 1, and with the same block descriptions operative as was present in FIG. 1, however the transmit interface 114 is directly coupled via leads 502/504 to a transmit transducer 524 and generating transmit beam 526, which is coincident on the surface with the receive beam profile 528 of receive transducer 530, which conveys the receive signal using leads 506/508 to receive amplifier 116, where the signal processing occurs as described previously for FIG. 1, however, the system of FIG. 5 operates continuously, with the transmitter continuously transmitting, and the receiver baseband signal being continuously received. This operation is advantageous for detection of signal bandwidth which exceeds the pulsed transmit configuration described in FIG. 3. Because the CW transmit signal results in a standing DC offset at the receive mixers 140 and 142, it is desired to provide electronic isolation between transmit element 524 and receive element 530. For the case of CW processing, the low pass filters 570 and 572 may set to the Nyquist rate of half of the transmit clock rate (Ftx/2), or they may alternatively be set to the highest response frequency expected during measurement, not to exceed Ftx/2. The advantage of matching the low pass filter 570 and 572 bandwidth to the signal bandwidth is the reduction in excess noise from out-of-band noise frequency contributions.

The systems of FIGS. 1, 2, and 5 may require the ultrasound transceiver radiation patterns (128 of FIGS. 1 and 2, 526 of FIG. 5) be visualized at the insonified surface of the membrane, so that the region of insonification which is being characterized may be easily identified visually. An optical illumination system (such as a collimated LED, laser, or other beam source) may be added to indicate the region being examined and characteristics by the system, such as by adding an optical source which converges or is co-linear with the radiation pattern 128 of FIGS. 1 and 526 of FIG. 5.

Figure 6:
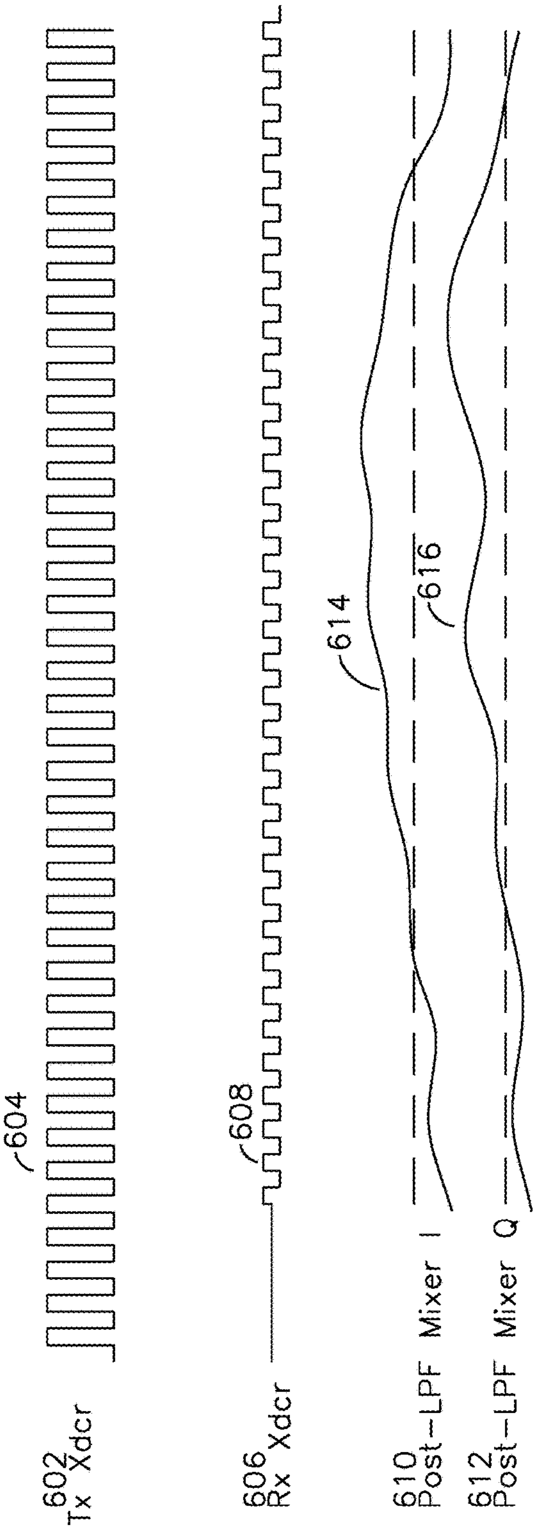
FIG. 6 shows the waveforms for the CW system of FIG. 5.

FIG. 6 shows waveform plots for the baseband CW system of FIG. 5. The system clock 110, transmit waveform generator 112, and transmit transducer interface 114 generate a DC-biased transducer CW signal waveform 602 of FIG. 6, which is applied to the transmit transducer 524 of FIG. 5, and the receive transducer 530 of FIG. 5 generates receive signal 608 of FIG. 6. A DC bias may be required for a cMUT transducer, whereas a piezoelectric transducer does not require a DC bias. The outputs of the I and Q channel low pass filters 136 and 138, respectively, are shown as waveforms 614 and 616. The phase unwrapping techniques described previously may be applied to these waveforms as well, where the detected phase crosses the +/−180° boundary and wraps to the opposite boundary.

Figure 7A:
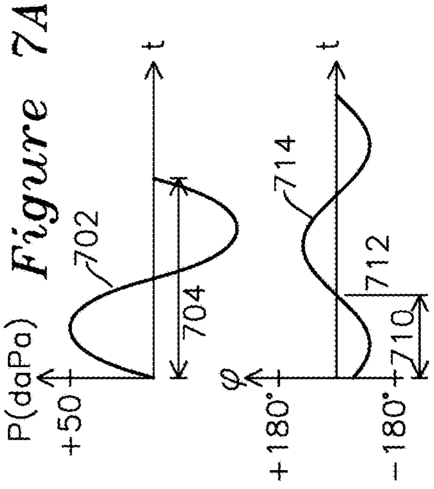
FIG. 7A is a plot of a sinusoidal excitation source and associated membrane or surface or membrane displacement response.
Figure 7B:
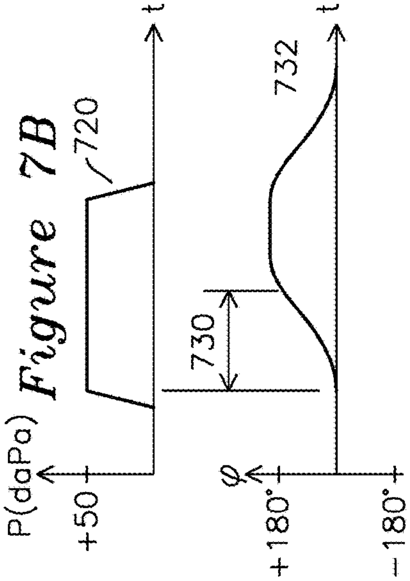
FIG. 7B is a plot of a step excitation source and associated membrane or surface or membrane displacement response.

FIGS. 7A and 7B show CW output 714 for an excitation 702, and the sample points of 332 and 372 of FIGS. 4A and 4B are not present, as the CW system of FIG. 5 is not subject to the baseband Nyquist sampling limitations of the pulsed dopper system of FIGS. 2 and 3, provided that the mixer output is sampled at a sufficiently high rate to satisfy the Nyquist criteria for phase changes at the mixer output.

The transducer types for 130 of FIGS. 1 & 2, and 524 and 530 of FIG. 5A may be any of capacitive micromachined ultrasonic transducer (cMUT), or piezoelectric transducers, for example, formed with the piezoelectric material PZT.

The example embodiments for the signal processors have shown embodiments of a pulsed Doppler system of FIGS. 1 and 2, and a CW Doppler system of FIG. 5. Each of these systems can be practiced using direct RF sampling, as shown in FIG. 2, where a bandpass filter is operative to reduce the noise bandwidth of the system to $e_n=\sqrt{4KTBR}$, commonly expressed as nanovolts per root hertz, where K is the Boltzmann constant $1.38*10^{-23}$;

T is the temperature of the system, assumed to be 300° K;

B is the bandwidth of the sampled signal (either the bandwidth of the bandpass filter 236 of FIG. 2, or bandwidth of the low pass filter 136/138 of FIGS. 1 and 5;

and R is the resistance generating the Johnson noise, typically 50 ohms.

In an ideal system Johnson noise is generated by transducer 160 and preamplifier 120 of FIG. 1, and this noise is frequency-limited to reduce its effect on system measurements. The noise floor for a 50 ohm system is 0.9 nV/$\sqrt{\text{Hz}}$. It is typically easier to perform narrowband filtering on a baseband signal such as the low pass filters 136 and 138 of FIG. 1 than the bandpass filter 236 of FIG. 2. For example, a first order band pass filter 236 for a 1.5 MHz system might have a 3 db bandwidth of 1 MHz, whereas the desired signal content is below 1 KHz, which is difficult to incorporate into bandpass filter 236, but simple to incorporate into low pass filter 136. Accordingly, the sample noise floor for 1 KHz baseband system would 28 nV rms whereas the 1 MHz bandwidth direct sampling system would be 30× higher, or 900 nV rms with the same signal energy. The noise factor of the system (typically governed by the first few elements in the receive chain) is managed separately, as it would scale the noise floor by the noise factor, so a 6 dB noise factor would approximately double both of the above rms noise floor values.

The invention may be practiced many different ways. In one embodiment, the phase and amplitude analyzer produces an elasticity metric which is a characterization of the sequence of phase measurements from the ultrasound reflection from the surface in combination with the displacement of the surface from the surface excitation source. The elasticity metric which is derived from the response of the surface may provide an indication of several different phenomenon. The elasticity metric may indicate whether a surface adjacent to a membrane has a gaseous boundary (in which case the reflection is from the membrane itself) or fluid boundary (in which case the reflection is from both the membrane and fluid adjacent to the membrane). The elasticity metric may indicate, for the case of characterizing a fluid behind the membrane fluid boundary, the extents or characteristics of the fluid, or alternatively it may provide a means to measure the characteristics of an elastic fluid with or without hysteresis of response, whereby the fluid has an offset in displacement response, or "memory", such that the response behavior in one direction is similar to the response behavior in the opposite direction, but only after traveling a particular displacement distance. For a hysteresis response, it may be necessary to characterize the linear behavior of the response after a particular measured displacement associated with the hysteresis of the system. A fluid elasticity metric may be determined from the characteristic response of the surface or membrane to the surface excitation and reflected ultrasound characterization.

The components of the system are shown in block diagram form for clarity in understanding the invention. It should be understood that the physical components of the invention may be located anywhere, including adjacent to the surface to be measured or any distance from that surface. The particular arrangement of the elements with respect to the surface or membrane to be measured is shown for clarity and to illustrate one example of the invention.

The excitation generator may be a air bladder manipulated by an operator to apply a force to a membrane or surface, an air displacement generator producing alternating pressure, step pressure, or air puffs. The excitation generator output may be sealed to the surrounding region of the surface or unsealed and using a puff of gas such as atmospheric air or other suitable gas.

The estimate of surface deflection may be derived from a measured estimate of velocity, an acceleration, or any other metric associated with deflection over time. In one example of the invention, the excitation is a step or impulse response with a rising edge, falling edge, or impulsive excitation which includes decomposed frequency content which is greater than the expected response frequency of the system, and the estimate of elasticity or viscosity is performed by examination of a ringdown characteristic. In another example of the invention, the ringdown characteristic comprises at least one of an exponential decay time or a ring cycle interval or frequency, such as the decomposition of a response into a ringdown characteristic, such as:

$$\phi(t) = e^{-t/\tau}\cos\left(2\pi \int t\right)$$

where:

$\phi(t)$ is the captured phase for a series of measurements;

$\tau$ is the exponential decay coefficient;

f is the ring cycle frequency; and t is time.

In one example of a non-contact elasticity measurement, the excitation generator is an air puff directed through a nozzle to a membrane surface, the membrane having an underlying liquid to be characterized. The liquid may be a semi-solid food item such as yogurt, cheese, or other fermented item, and the elasticity measurement may provide a measurement of completion of a fermentation or other time-dependent process.

In another example of the invention, the excitation generator is an air puff coupled to the surface of a semi-solid food item being fermented or cured, such as one using a bacterial or other time-dependent process, and the ultrasound transducer periodically receives a reflected signal from an ultrasound transmit event, where the received amplitude or phase during the relaxation time of the food item after the air puff excitation is compared to the originally transmitted signal to characterize the time-dependent displacement characteristic of the food item to derive an elasticity or other physical property based on the relaxation time change in response to the excitation.

In another example of the invention, the excitation generator applies an impulsive pressure to the surface of a food item such as a vegetable or fruit, the ultrasound energy applied to the food item being reflected and characterized to measure the time dependent surface response of the fruit or vegetable, thereby using the reflected phase or amplitude response during a surface relaxation time to determine an elasticity or other physical property which may be correlated to the ripeness of the fruit or vegetable. In one example of the invention, the food item may be placed into a holder and the surface excited with a puff of gas such as air, the surface deflection response estimating ripeness or other property. In another example of the invention, the excitation may be a gas which is delivered at a supersonic velocity and/or at a glancing angle to the surface of the food item, or one or more food items may be placed into a chamber which has a variable pressure to measure a low frequency surface response to pressure, such as deflection vs. pressure. In another aspect of the invention, the excitation may be applied to one surface and the response measured on a different surface of the same item, such as the measurement of a propagating surface wave or a shear wave which travels through the item being characterized.

In another example of the invention, the excitation generator applies an impulsive pressure to an animal or human organ such as the eye during an interval when ultrasound energy is applied to the eye, the phase changes of the reflected ultrasound during application of the non-contact excitation or after removal of the non-contact excitation indicating an elasticity which may be correlated to an inter-ocular pressure for measurement or diagnosis of glaucoma.

In another example of the invention, the excitation may be an air puff containing nitrogen (N2) or other non-reactive gas such as Argon, Carbon Dioxide (CO2), Helium (He), or an inert gas to prevent oxidation of the membrane of surface to be characterized. For these alternative gasses, the acoustic wave velocity will have a different value compared to the velocity of air.

In another example of the invention, the ultrasound transducer is formed by a plurality of membrane surfaces which are each electrostatically excited by a transmit voltage waveform to cause the membrane surface to form and transmit an acoustic wave, such as a capacitive micromachined ultrasound transducer (CMUT). The applied voltage waveform may also include a direct current (DC) component for positioning the membrane surface in a desired range of motion, while the alternating current (AC) component of the applied voltage waveform may provide movement of the membrane for generation of ultrasound energy.

In another example of the invention, the ultrasound transducer may be a ceramic piezoelectric transducer which changes mechanical shape based on the applied voltage.

Various aspects of the invention may be practiced, as recited below:

A signal processor for detection of air or fluid behind a surface, and further estimating an elasticity metric of a fluid when present, the signal processor comprising:

an ultrasound transducer for coupling ultrasound energy to a surface;

an excitation generator producing sub-audio, audio, or super-audio excitation coupled into a surface to me measured to cause a measurable deflection in a surface a transmitter coupled to the ultrasound transducer during a transmit interval;

a receiver coupled to the ultrasound transducer during a receive interval which follows the transmit interval;

a phase and/or amplitude analyzer comparing the phase of a transmit signal of the transmit interval to a phase and/or amplitude of a receive signal during the receive interval to estimate a surface deflection;

the signal processor deriving a metric from the phase and amplitude analyzer by comparing the surface deflection with the excitation generator output;

the elasticity metric indicating whether the receive signal is a reflection from a surface which includes reflections from air or from fluid, and optionally characterizing a fluid from the surface deflection characteristic.

A signal processor where the excitation generator generates at least one of: sinusoidal, impulse, steady state, or periodic sub-audio, audio, or super-audio excitation.

A signal processor where the phase and amplitude analyzer is operative on received acoustic energy from the transducer at a natural center frequency of the transducer.

A signal processor where the phase and amplitude analyzer is operative on received acoustic energy from the transducer at a baseband frequency spectrum, the baseband frequency spectrum formed by mixing the receive signal with a carrier frequency which is at substantially the center frequency of the transmitter.

A signal processor where the transmitter generates a transmit waveform which includes an excitation voltage signal at a center frequency of the transducer during the transmit interval.

A signal processor where the sum of the transmit interval and the receive interval is greater than 50 microseconds and less than 1 millisecond.

A signal processor where the phase and amplitude analyzer determines a weighted or unweighted average phase with respect to a transmit clock.

A signal processor where a metric is derived from a temporal phase change between a received signal from the transducer during the receive signal interval and a transmit clock which is operative during the receive interval.

A signal processor where a metric is derived from a phase relationship between a mixer output baseband signal and the excitation generator output.

A signal processor where a metric is derived from a temporal phase change in the receive signal and an excitation generator output.

A signal processor where the ultrasound transducer generates a periodic burst of transmit signal energy.

A signal processor where the ultrasound transducer generates continuous transmit signal energy.

A signal processor where the phase and amplitude analyzer is operative on received signals to identify a region of first reflection from a membrane or surface, and thereafter characterizes a fluid behind an identified region as either air or liquid.

A signal processor where, when the fluid behind an identified region is liquid, determines a surface elasticity, or fluid viscosity using a phase and amplitude response associated with a measurable deflection.

A signal processor for characterizing a temporal response from a surface or membrane, the signal processor having:
- an excitation generator producing sub-audio, audio, or super-audio excitation for application to a surface or membrane to cause a displacement;
- a transducer for launching acoustic waves towards a surface to be characterized and receiving reflections from the surface;
- a visual indicator to allow the direction of acoustic waves from the transducer to a region of interest on the surface;
- an ultrasound transmitter operative during a transmit interval and coupling a gated frequency burst to the transducer;
- an ultrasound receiver operative during a receive interval and coupled to the transducer;
- a phase and amplitude detector comparing the phase of a transmit clock to a receive signal from the ultrasound receiver and generating a phase output;
- a response analyzer comparing the phase output to the excitation generator output, the response analyzer determining a viscosity of a fluid adjacent to surface to be characterized by comparison of the phase output and the excitation generator output.

A signal processor where the transducer is at least one of a capacitive micro-machined ultrasound transducer (cMUT) or a piezoelectric transducer.

A signal processor where the excitation generator is at least one of a voice coil actuator, or a moving diaphragm.

A signal processor where the visual guide is at least one of: a laser diode, light emitting diode, or optical indicator which illuminates a region corresponding to a beam profile from the ultrasonic transducer.

A signal processor where the ultrasound transmitter has a repetition rate of less than 15 KHz.

A signal processor where the phase and amplitude detector is a baseband mixer generating an output after a low pass filter.

A signal processor where the phase and amplitude detector is operative at a center frequency of the transducer.

A signal processor where the response analyzer compares the phase output and the excitation generator output over a plurality of sample points over a duration of time when the excitation generator is operative.

A signal processor where the receive interval and the transmit interval are concurrent intervals.

A signal processor where the receive interval and the transmit interval are exclusive intervals.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for non-contact measurement of an elastic surface, the method comprising:
- (a) providing a non-contact force to a surface or a volume of material adjacent to the surface to be characterized using an excitation generator, wherein the non-contact force comprises a step or impulse pressure; and
- (b) in response to the non-contact force, forming a displacement measurement, the displacement measurement comprising:
  - (i) directing a transmit burst of ultrasound energy from a transducer to the surface or the volume of material adjacent to the surface;
  - (ii) receiving a reflected ultrasound energy from the surface or the volume of material adjacent to the surface with the transducer;
  - (iii) setting a range gate for a first region of the reflected ultrasound energy; and
  - (iv) distinguishing a movement or displacement of the first region from a movement or displacement of a second region based at least in part on the range gate.

2. The method of claim 1, wherein the transmit burst has a spatial extent which matches a region of the surface or the volume of material adjacent to the surface which is moving in a same direction as the transmit burst.

3. The method of claim 1, wherein the transmit burst comprises a transmitted ultrasound energy; and wherein setting the range gate is based at least in part on at least one of: a frequency of the transmitted ultrasound energy, a propagation velocity of the transmitted ultrasound energy, or a number of cycles of the transmitted ultrasound energy.

4. The method of claim 1, further comprising, when the surface or the volume of material adjacent to the surface moves out of a range of a first range gate associated with a first depth to a second depth, adaptively forming a displacement measurement based at least in part on a second displacement measurement comprising a second range gate associated with the second depth.

5. The method of claim 1, wherein the method further comprises: comparing a phase of a transmitted ultrasound energy of the transmit burst to the reflected ultrasound energy to form a displacement estimate for the surface or the volume of material adjacent to the surface; and forming an estimate of an elasticity of the surface or a viscosity of the volume of material adjacent to the surface based at least in part on a series of displacement measurements.

6. The method of claim 1, wherein providing the non-contact force comprises directing a puff of air to the surface or to the volume of material adjacent to the surface.

7. The method of claim 1, wherein the transducer comprises a capacitive micromachined ultrasonic transducer (cMUT) or a piezoelectric transducer.

8. The method of claim 1, wherein the surface comprises a membrane over a fluid.

9. The method of claim 1, wherein the surface comprises a solid or semi-solid food item.

10. The method of claim 4, wherein the displacement measurement for the surface or the volume of material adjacent to the surface is based at least in part on a reflected Doppler ultrasound signal.

11. A method for non-contact measurement of an elastic surface, the method comprising:

(a) providing a non-contact force to a surface or a volume of material adjacent to the surface to be characterized using an excitation generator, wherein the non-contact force comprises a step or impulse pressure;

(b) in response to the non-contact force, forming a displacement measurement;

(c) forming an estimate of elasticity based at least in part on the displacement measurement; and (d) characterizing the surface or the volume of material adjacent to the surface based at least in part on the estimate of elasticity, wherein the characterizing is based at least in part on a hysteresis response of the surface or the volume of material adjacent to the surface.

12. The method of claim 11, wherein (b) further comprises (i) directing a transmitted ultrasound energy from a transducer to the surface or the volume of material adjacent to the surface;

(ii) receiving a reflected ultrasound energy from the surface or the volume of material adjacent to the surface with the transducer; and (iii) comparing a phase of the transmitted ultrasound energy to the reflected ultrasound energy to form a displacement estimate for the surface or the volume of material adjacent to the surface.

13. The method of claim 11, wherein characterizing the surface or the volume of material adjacent to the surface based at least in part on the hysteresis response is based at least in part on an offset in the displacement measurement from another displacement measurement.

14. The method of claim 13, wherein the offset comprises a first displacement response in a first direction and a second displacement response in a second direction, wherein the first direction is opposite to the second direction, and wherein the first displacement response is similar to the second displacement response after the first displacement response travels a displacement distance.

15. The method of claim 11, further comprising characterizing the surface or the volume of material adjacent to the surface based at least in part on a series of hysteresis responses of a series of displacement estimates.

16. The method of claim 15, further comprising forming the series of hysteresis responses based at least in part on a linear behavior of each hysteresis response of the series of hysteresis responses.

17. The method of claim 11, wherein the volume of material adjacent to the surface comprises a fluid having an elasticity.

18. The method of claim 11, wherein providing the non-contact force to the surface or to the volume of material adjacent to the surface comprises directing a puff of air to the surface or to the volume of material adjacent to the surface.

19. The method of claim 12, wherein the transducer comprises a capacitive micromachined ultrasonic transducer (cMUT) or a piezoelectric transducer.

20. The method of claim 11, wherein the surface comprises a solid or semi-solid food item.

21. The method of claim 12, wherein the displacement estimate for the surface or the volume of material adjacent to the surface is based at least in part on a reflected Doppler ultrasound signal.

* * * * *